US006990176B2

(12) United States Patent
Sherman et al.

(10) Patent No.: US 6,990,176 B2
(45) Date of Patent: Jan. 24, 2006

(54) METHODS AND APPARATUS FOR TILEABLE SENSOR ARRAY

(75) Inventors: Donna Marie Sherman, East Greenbush, NY (US); William Edward Burdick, Jr., Niskayuna, NY (US); James Wilson Rose, Guilderland, NY (US)

(73) Assignee: General Electric Company, Niskayuna, NY (US)

( * ) Notice: Subject to any disclaimer, the term of this patent is extended or adjusted under 35 U.S.C. 154(b) by 256 days.

(21) Appl. No.: 10/697,515

(22) Filed: Oct. 30, 2003

(65) Prior Publication Data

US 2005/0094763 A1 May 5, 2005

(51) Int. Cl.
  *H05G 1/64* (2006.01)
  *G01T 1/24* (2006.01)
(52) U.S. Cl. ............... 378/98.8; 378/19; 378/161; 250/370.09
(58) Field of Classification Search .......... 378/19, 378/98.8, 161; 250/208.1, 370.08, 370.09, 250/370.1, 370.11
See application file for complete search history.

(56) References Cited

U.S. PATENT DOCUMENTS

| | | | | |
|---|---|---|---|---|
| 5,248,885 A | * | 9/1993 | Sato et al. ............. | 250/370.15 |
| 5,464,984 A | * | 11/1995 | Cox et al. ............... | 250/370.11 |
| 5,742,060 A | * | 4/1998 | Ashburn ................. | 250/370.09 |
| 6,396,898 B1 | * | 5/2002 | Saito et al. ..................... | 378/19 |
| 6,465,790 B1 | * | 10/2002 | Monnet et al. ......... | 250/370.09 |
| 6,510,195 B1 | * | 1/2003 | Chappo et al. ............... | 378/19 |
| 6,621,084 B1 | * | 9/2003 | Wainer et al. .......... | 250/370.09 |
| 6,819,001 B2 | | 11/2004 | Burdick, Jr. et al. | |
| 6,883,963 B2 | * | 4/2005 | Nolewaika ................... | 378/207 |
| 2004/0109299 A1 | | 6/2004 | Burdick, Jr. et al. | |

OTHER PUBLICATIONS

F. Quercioli, B. Tiribilli, A. Mannoni, and S. Accai, "Play Optics with LEGO™," Fifth International Topical Meeting on Education and Training in Optics, pp. 233-242 (1997).

* cited by examiner

Primary Examiner—Allen C. Ho
(74) Attorney, Agent, or Firm—Fletcher Yoder

(57) ABSTRACT

A detector array kit that includes at least one sensor array. The sensor array has an active side at least one sensor on the flat active side configured to detect a particular form of energy. The sensor array active side has a positioning structure on the active side that is essentially transparent to the particular form of energy. The positioning structure includes a plurality of spaced compressible posts or tubes configured to compressively and frictionally engage with a complementary mounting structure. The detector kit further includes a complementary mounting structure essentially transparent to the particular form of energy.

33 Claims, 9 Drawing Sheets

METHODS AND APPARATUS FOR TILEABLE SENSOR ARRAY

BACKGROUND OF THE INVENTION

This invention relates generally to electronic arrays, and more particularly, to methods and apparatus suitable for assembling accurately aligned electronic sensor arrays.

Electronic sensors and transmitters are often configured in arrays to transmit or receive data in a two dimensional format or to effect a desired resolution for a given area. For example, at least one known sensor includes a photodiode including an array of photosensitive pixels coupled to a scintillating medium, which can also be configured as an array of scintillator cells. When subjected to x-ray energy, the scintillator generates optical photons which in turn excite the underlying photosensitive pixels within the photodiode thereby producing an electrical signal corresponding to an incident photon flux.

Assembly of a computed tomographic (CT) detector array requires high precision alignment of more than 50 sensor elements. In at least one known system, a detector array comprises a plurality of sensor elements. Each sensor element in the known CT detector array comprises an x-ray scintillator deposited on an array of photodiode visible light sensors. Thus, sensor elements are referred to herein as "sensor arrays." Each sensor array must be aligned to an x-ray collimator structure as well as to its neighboring sensor arrays in the detector array. Such precise alignment requires overcoming a number of complications. Each sensor array has flat, parallel inner and outer faces and the sensor arrays are set against a curved collimator rail. Because the rail is curved, edges of the inner face of each sensor array (i.e., the face closest to the collimators and the x-ray source) are closer to adjacent sensor arrays than edges of the outer face. Detector arrays are tested after alignment and the sensor arrays comprising a detector array are bolted in place when testing is complete. Test results are used for iterations of swapping of sensor arrays to optimize overall performance. This swapping requires dismounting and subsequent realignment of sensor arrays in new positions along the collimator rail. Thus, alignment procedures tend to be expensive and time-consuming. Moreover, the procedures do not scale well to detector arrays comprising two-dimensional arrays of sensor arrays, for example, three adjacent rows of over 50 sensor elements.

BRIEF DESCRIPTION OF THE INVENTION

There is therefore provided, in some configurations of the present invention, a sensor array having an active side. The sensor array includes at least one sensor on the flat active side configured to produce a signal when a particular form of energy is detected. The sensor array further includes a positioning structure essentially transparent to the particular form of energy. The positioning structure includes a plurality of spaced compressible posts or tubes configured to compressively and frictionally engage with a complementary mounting structure.

Some configurations of the present invention provide a detector array kit. The detector array kit includes at least one sensor array. The sensor array has an active side at least one sensor on the flat active side configured to detect a particular form of energy. The sensor array active side has a positioning structure on the active side that is essentially transparent to the particular form of energy. The positioning structure includes a plurality of spaced compressible posts or tubes configured to compressively and frictionally engage with a complementary mounting structure. The detector kit further includes a complementary mounting structure essentially transparent to the particular form of energy.

Still other configurations of the present invention provide a detector array kit. The detector array kit includes a plurality of sensor arrays each having an active side. Each sensor array has least one sensor on its active side configured to detect a particular form of energy. The sensor arrays further include a positioning structure on the active side that is essentially transparent to the particular form of energy on their flat sides, wherein the positioning structure includes a plurality of spaced compressible posts or tubes configured to compressively and frictionally engage with a complementary mounting structure. The detector array kit also includes a unitary complementary mounting structure essentially transparent to the particular form of energy and having a plurality of planar segments that meet at angles.

Still other configurations of the present invention provide a computed tomograpic imaging apparatus that includes a rotating gantry, an x-ray source on the rotating gantry configured to project an x-ray beam through an object being imaged, a table configured to support the object in the x-ray beam, and a detector array on the rotating gantry configured to detect x-rays passing through the object. The detector array includes a plurality of sensor arrays each having an active side and at least one x-ray sensor on the active side configured to detect x-rays. The sensor arrays each also have a positioning structure on the active side that is essentially transparent to the particular form of energy. The positioning structure includes a plurality of spaced compressible posts or tubes configured to compressively and frictionally engage with a complementary mounting structure. The detector array further includes a unitary complementary mounting structure essentially transparent to x-rays and having a plurality of planar segments that meet at angles.

Still other configurations of the present invention provide a method for repairing a detector array. The method includes disengaging a first sensor array having an active side and at least one sensor on the active side configured to produce a signal when a particular form of energy is detected. The sensor array also includes a positioning structure on the active side that is essentially transparent to the particular form of energy. The positioning structure includes a plurality of spaced compressible posts or tubes compressively and frictionally engaged with a complementary mounting structure essentially transparent to the particular form of energy. The method further includes compressively and frictionally engaging a second sensor array in place of the first sensor array.

It will be recognized that configurations of the present invention facilitate insertion and extraction or field replacement of sensor arrays in a detector array with high dimensional accuracy, even without the use of special tools or extra attachment components. Furthermore, some configurations of the present invention facilitate insertion and extraction or field replacement of sensor arrays in two dimensional detector arrays. High dimensional accuracy can be achieved at relatively low cost and in high production volumes.

DETAILED DESCRIPTION OF THE INVENTION

Figure 1:
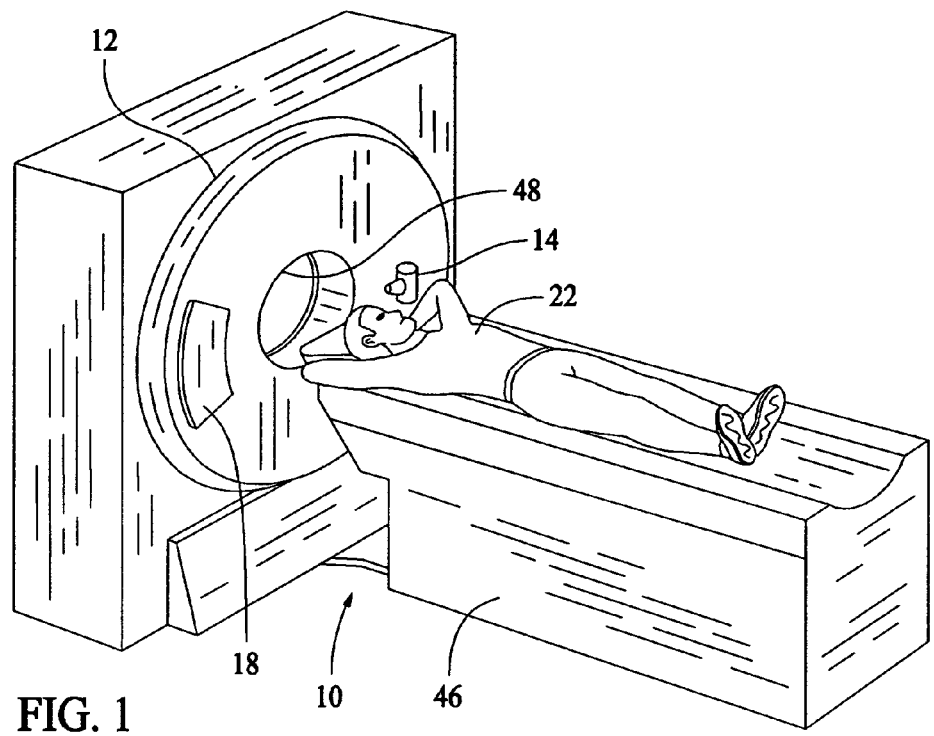
FIG. 1 is a pictorial view of a CT imaging system.

As used herein, a "sensor array" refers to a component comprising one or more individual sensors. In many configurations, a sensor array may itself comprise a component having a two-dimensional array of sensors, and a plurality of sensor arrays may be assembled into a larger assembly referred to as a "detector array." A "sensor array" may comprise an M×N array of sensors, wherein both M or N are equal to or greater than one. Thus, the scope of the term "sensor array" is not intended to exclude devices having only one sensor.

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each sensor of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical, weighting scheme, a method can be derived to multiply the weight with the projection data prior to the filtered backprojection algorithm.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 2:
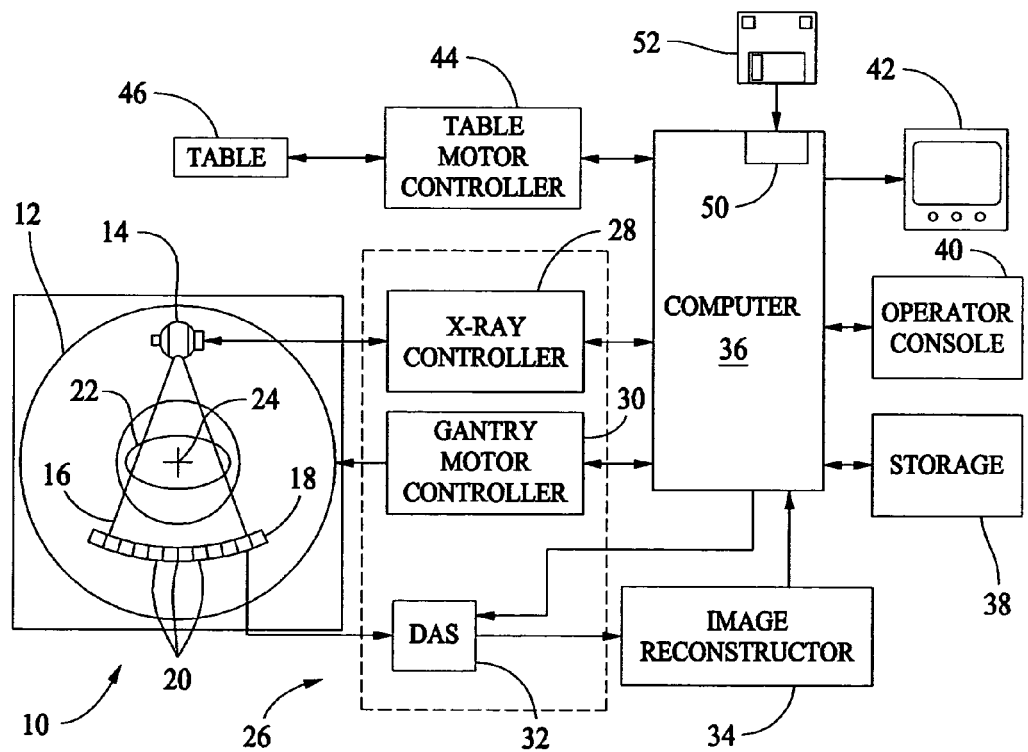
FIG. 2 is a block schematic diagram of the system illustrated in FIG. 1.

Referring to FIGS. 1 and 2, a multi-slice scanning imaging system, for example, a Computed Tomography (CT) imaging system 10, is shown as including a gantry 12 representative of a "third generation" CT imaging system. Gantry 12 has an x-ray tube 14 (also called x-ray source 14 herein) that projects a beam of x-rays 16 toward a detector array 18 on the opposite side of gantry 12. Detector array 18 is formed by a plurality of detector rows (not shown) including a plurality of sensors 20 which together sense the projected x-rays that pass through an object, such as a medical patient 22 between array 18 and source 14. Each sensor 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of sensors 20 (i.e., a detector row). However, multi-slice detector array 18 includes a plurality of parallel detector rows of sensors 20 such that projection data corresponding to a plurality of quasi-parallel or parallel slices can be acquired simultaneously during a scan.

Rotation of components on gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from sensors 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or another digital source such as a network or the Internet, as well as yet to be developed digital means. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. Although the specific embodiment mentioned above refers to a third generation CT system, the methods described herein equally apply to fourth generation CT systems (stationary detector—rotating x-ray source) and fifth generation CT systems (stationary detector and x-ray source). Additionally, it is contemplated that the benefits of the invention accrue to imaging modalities other than CT. Additionally, although the herein described methods and apparatus are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center.

Figure 3:
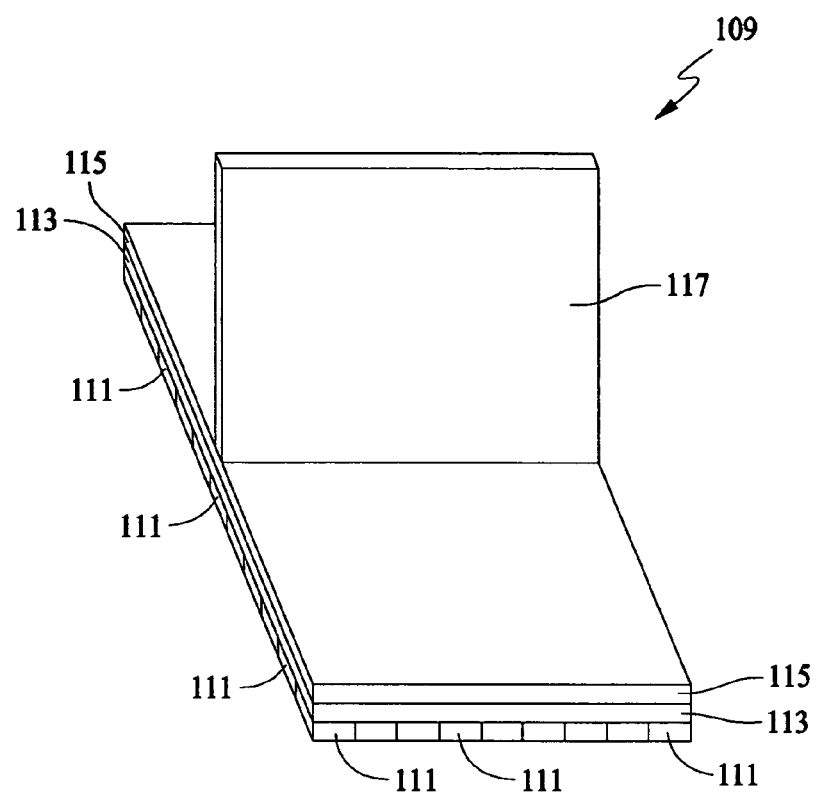
FIG. 3 is a pictorial view of a portion of a sensor/transmitter array.
Figure 4:
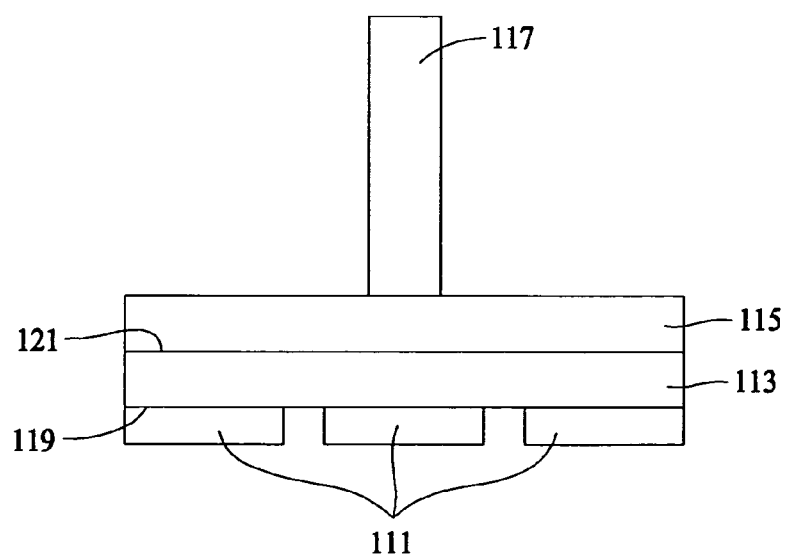
FIG. 4 is a side view of a portion of the transducer array shown in FIG. 3.

FIG. 3 is a portion of a tileable sensor array 109 that can be used with a system, such as, but not limited to a computed tomography imaging system, a magnetic resonance imaging system, a Positron Emission Tomography (PET) system, and a multi-energy computed tomography imaging system. FIG. 4 is a side view of a portion of sensor array 109 shown in FIG. 3. Transducer, as used herein, describes a device for converting at least one of a sound, a temperature, a pressure, a light or other signal to or from an electronic signal. In an exemplary embodiment, sensor array 109 includes a plurality of transducers 111 configured to receive an input signal and transmit a desired electrical output signal. For example, transducer array 109 includes a plurality of sensor devices, such as, but not limited to, a photodiode, a back-illuminated photodiode, a sonic sensor, i.e. a sensor configured to detect sounds, a temperature sensor, and an electromagnetic radiation sensor.

In an exemplary embodiment, sensor array 109 includes a plurality of transducers 111 fabricated on a substrate 113. In one embodiment, sensor array 109 includes an interposer 115, and an electronic device 117, electrically coupled to interposer 115. In another embodiment, electronic device 117 is electrically coupled to substrate 113 without using interposer 115. In an exemplary embodiment, transducers 111 are fabricated on a first side 119 of substrate 113 and at least one of interposer 115 and electronic device 117 are electrically coupled to a second side 121 of substrate 113.

Figure 5:
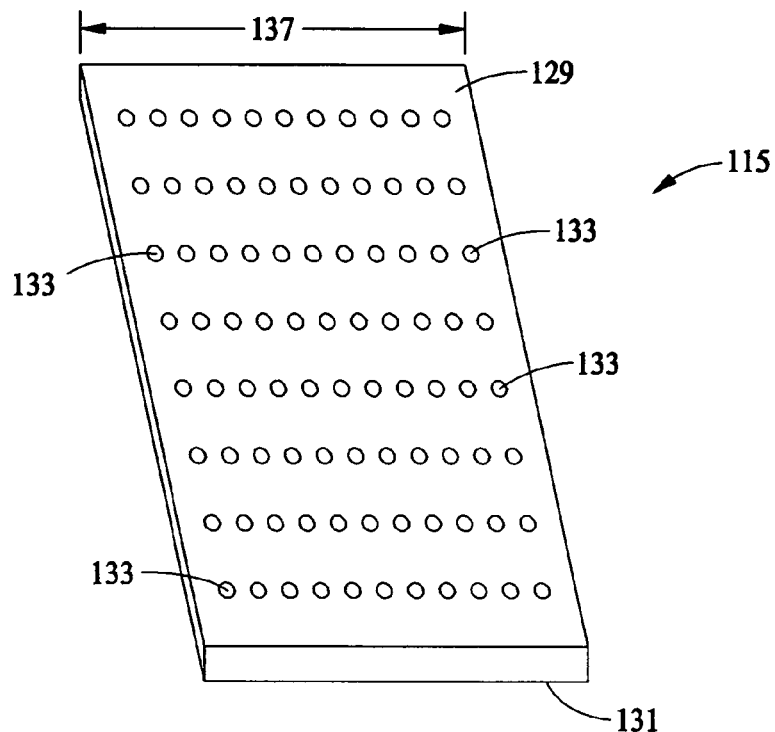
FIG. 5 is a perspective view of a first side of an interposer.
Figure 6:
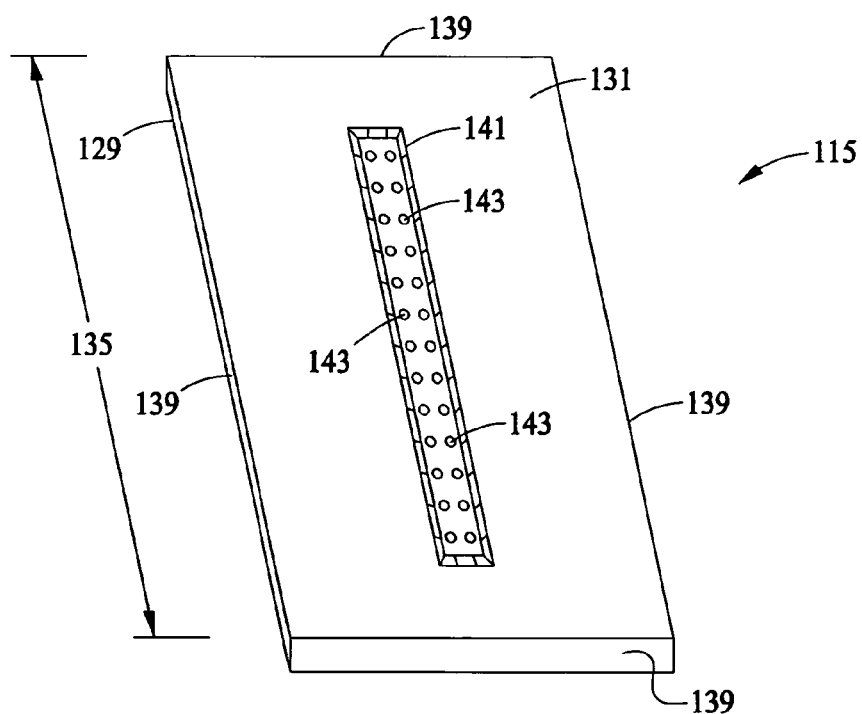
FIG. 6 is a perspective view of a second side of the interposer shown in FIG. 5.

FIG. 5 is a perspective view of a first side 129 of interposer 115. FIG. 6 is a perspective view of a second side 131 of interposer 115. Interposer first side 129 includes a plurality of input/output (I/O) connectors 133. In an exemplary embodiment, substrate 113 includes a plurality of I/O connectors (not shown) arranged such that an electrical connection is made between a desired I/O connector 133 on interposer first side 129, and a corresponding desired I/O connector positioned on substrate second side 121. Accordingly, substrate second side 121 is electrically coupled to interposer first side 129 using I/O connectors 133 and the I/O connectors positioned on substrate second side 121. Interposer 115 also includes a length 135 and a width 137. In one embodiment, length 135 and a width 137 are approximately equal to a length and width of substrate 113. In another embodiment, length 135 and a width 137 are less than a length and width of substrate 113 thereby providing maximum density of sensor arrays and clearance for subsequent assembly processes. In one embodiment, interposer second side 131 includes at least one electrical connector or socket 141. Socket 141 includes a plurality of input/output connectors 143, wherein each electrical connector 143 is electrically coupled to at least one electrical connector 133 on interposer first side 129. In an exemplary embodiment, interposer 115 includes a multilayer interconnect system including a plurality of input/output connectors on first side 129 electrically coupled to input/output connectors 143 on interposer second side 131 such that when an electrical signal is received at either input/output connectors 133 or 143, the electrical signal is passed to a corresponding input/output connector 133 or 143 on the opposite side of the interconnect system 115.

In one embodiment, input/output connectors 133 are permanently coupled to corresponding I/O connections positioned on substrate 113 using at least one of the attach methods of solder, an anisotropic conductive film (ACF) or paste (ACP), an ultrasonic bonding, a thermosonic bonding, and a thermocompression bonding. In another embodiment, input/output connectors 133 are removably coupled to corresponding I/O connections positioned on substrate 113 using a temporary connection, such as, but not limited to, a thermoplastic adhesive including embedded conductive contacts, a plurality of carbon nanofibers/tube, a low temperature solder, an elastomeric connector, and a metal plated or bumped flex.

In one embodiment, interposer 115 is a flexible interconnect fabricated from a material such as, but not limited to, metal-on-polyimide, an aramid, a fluorocarbon, and a polyester. Fabricating interposer 115 from a flexible material facilitates utilization of a minimum of geometry/features and multilayer, metal interconnects.

Figure 7:
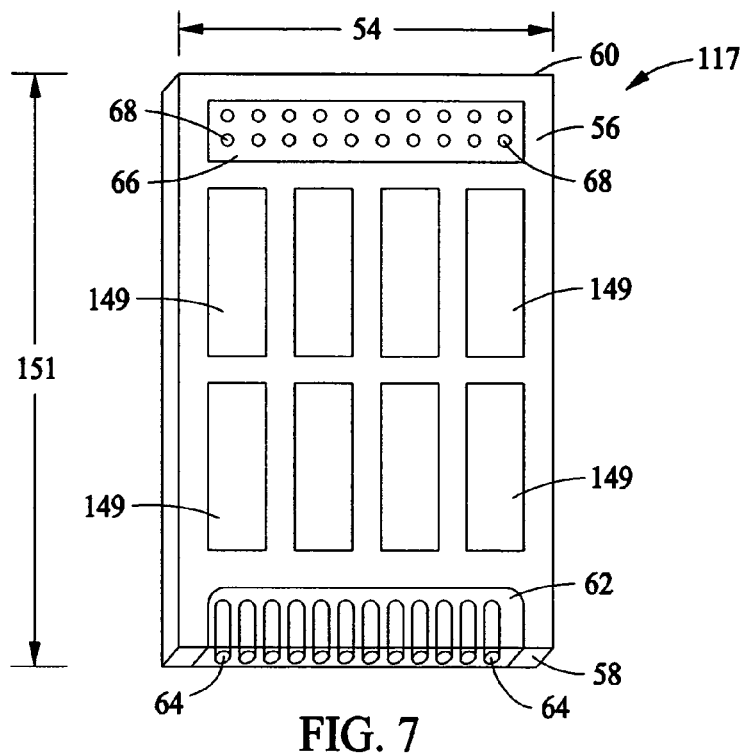
FIG. 7 is a perspective view of an electronic device.

FIG. 7 is a perspective view of electronic device 117. In an exemplary embodiment, electronic device 117 includes a plurality of signal processing circuits 149. Electronic device 117 also includes a length 151, a width 54, a first side 56, a first edge 58, and a second edge 60. In one embodiment, first edge 58 includes an electrical connector 62, including a plurality of input/output connectors 64 configured to electrically couple to associated input/output connectors 143 in socket 141. Electronic device 117 also includes an electrical connector 66 positioned on first side 56. In an exemplary embodiment, electrical connector 62 is implemented using a flexible printed circuit. Electrical connector 66 includes a plurality of input/output connectors 68 configured to electrically couple to associated input/output connectors 64, through circuits 149, on electronic device 117. In an exemplary embodiment, electronic device 117 and interposer 115 are removably coupled using socket 141 and electrical connector 62. In another embodiment, electronic device 117 is permanently coupled to interposer 115. In one embodiment, electronic device 117 is coupled to interposer 115 such that electronic device 117 is substantially orthogonal to interposer 115. Electronic device 117 also includes a flexible circuit (not shown) electrically coupled to electrical connector 66. In an exemplary embodiment, the flexible circuit is a flexible electrical cable including a plurality of electrical conductors, such as, but not limited to, a flexible ribbon cable.

Figure 8:
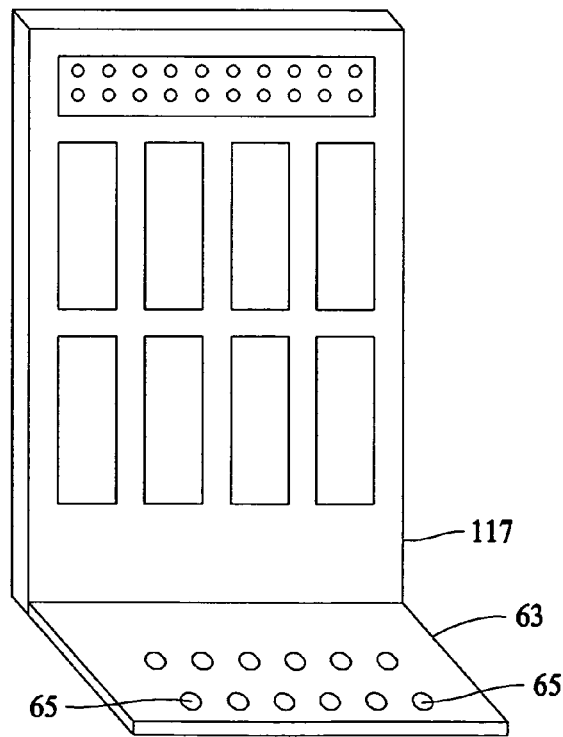
FIG. 8 is a perspective view of an alternate embodiment of the electronic device shown in FIG. 7.

FIG. 8 is a perspective view of an alternate embodiment of an electronic device 117 including an electrical connector 63 including a flexible printed circuit (not shown) that extends beyond first edge 58. Flexible circuit 63 includes a plurality of input/output connectors 65 configured to electrically couple to associated input/output connectors positioned on substrate second side 121. In this embodiment interposer 115 has been eliminated.

Figure 9:
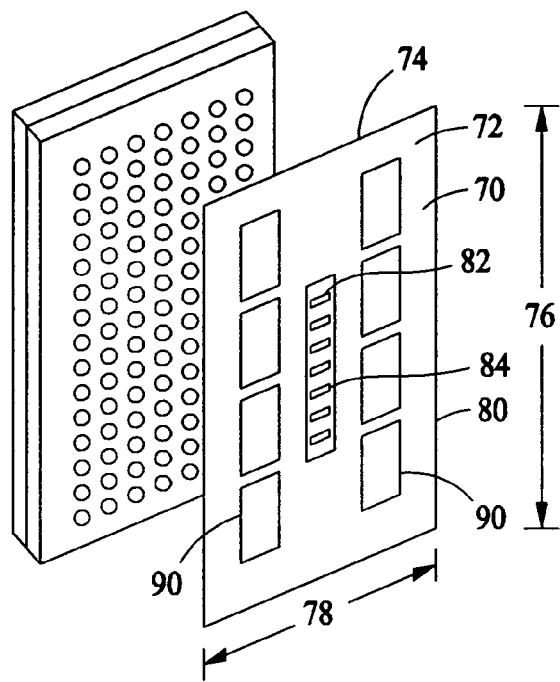
FIG. 9 is a perspective view of an interposer.

FIG. 9 is a perspective view of a rigid interposer 70. Interposer 70 includes a first side 72 and a second side 74. Interposer first side 72 includes a plurality of input/output (I/O) connectors (not shown) arranged such that an electrical connection is made between the desired I/O connector, on interposer first side 70, to the desired I/O connector on substrate second side 121. Accordingly, substrate second side 121 is electrically coupled to interposer first side 72 using the I/O connectors positioned on interposer 70 and the I/O connectors positioned on substrate second side 121. Interposer 70 also includes a length 76 and a width 78. In one embodiment, length 76 and a width 78 are approximately equal to a length and width of substrate 113. In another embodiment, length 76 and a width 78 are less than a length and width of substrate 113 thereby providing maximum density of sensor arrays and clearance for subsequent assembly processes Interposer first side 72 includes at least one electrical connector or socket 82. Socket 82 includes a plurality of input/output connectors 84, wherein each electrical connector 84 is electrically coupled to at least one electrical connector on interposer first side 72, i.e. interposer 70 is a multilayer interconnect system including a plurality of input/output connectors on first side 72 electrically coupled to the input/output connectors positioned on substrate second side 121 such that when an electrical signal is received at either the input/output connectors on interposer 70 or the input/output connectors on substrate second side 121, the electrical signal is passed to a corresponding input/output connector on the opposite side of interposer 70. In one embodiment, interposer 70 includes a plurality of signal processing circuits 90 positioned approximately parallel to interposer first side 72.

In one embodiment, the input/output connectors on interposer second side 74 are permanently coupled to the corresponding I/O connections positioned on substrate 113 using at least one of the attach methods of solder, an anisotropic conductive film (ACF) or a paste (ACP), an ultrasonic bonding, a thermosonic bonding, and a thermocompression bonding. In another embodiment, the input/output connectors on interposer second side 74 are removably coupled to corresponding I/O connections positioned on substrate 113 using a temporary connection, such as, but not limited to, a thermoplastic adhesive including embedded conductive contacts, a plurality of carbon nanofibers/tube, a low temperature solder, an elastomeric connector, and a metal plated or bumped flex.

Figure 10:
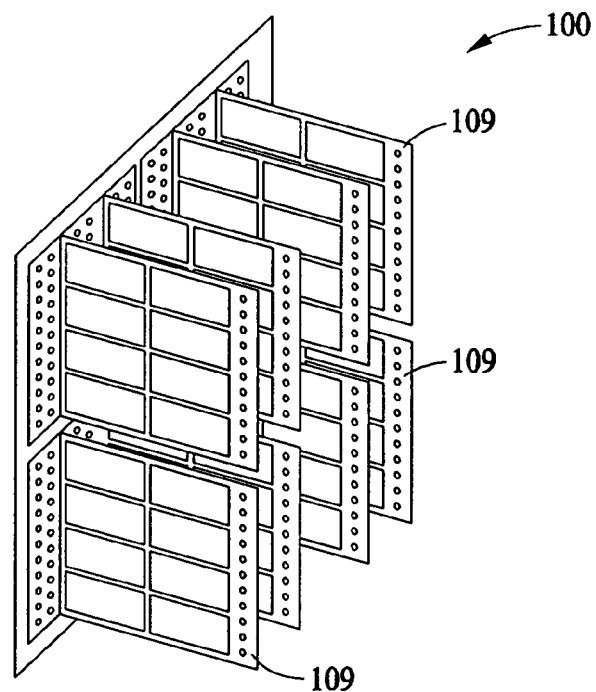
FIG. 10 is a pictorial view of a plurality of a sensor/transmitter arrays.

FIG. 10 is a pictorial view of a sensor array 100 including a plurality of sensor arrays 109. As shown, sensor arrays 109 are arranged in a two-dimensional array. In an exemplary embodiment, sensor array 100 can be configured to any size or dimension, relative to the quantity and arrangement of rows and columns of individual sensors, thus providing for desired structures compatible with applications in imaging or characterizing desired physical areas or volumes of physical objects, energy fields, image resolution, etc. One exemplary embodiment of a sensor array is a two dimensional configuration structured to approximate a curved surface.

Figure 11:
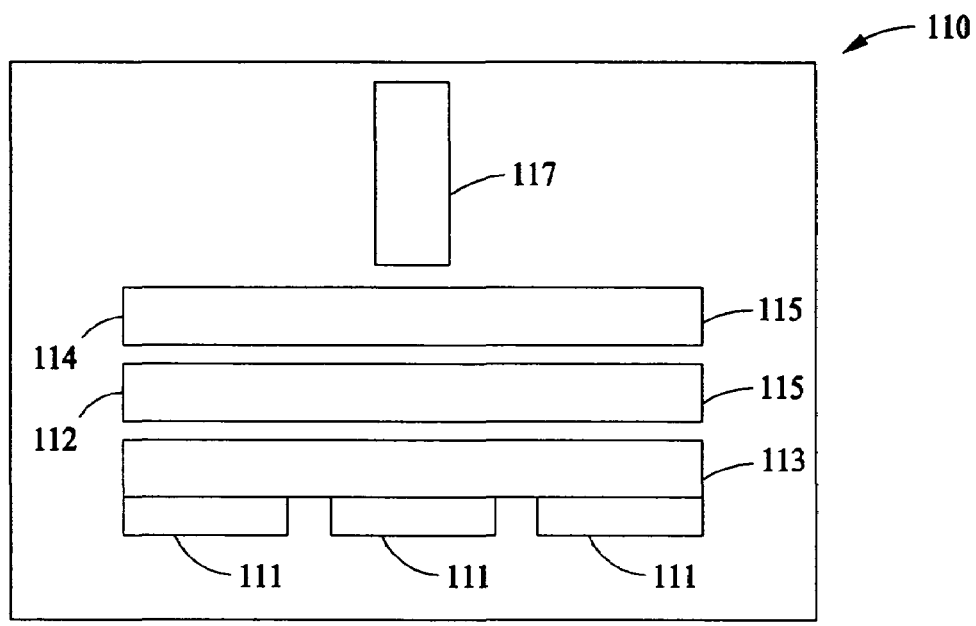
FIG. 11 is a top plan view of a first transducer array kit.

FIG. 11 is a top plan view of a sensor array kit 110. In an exemplary embodiment, sensor array kit 110 includes a plurality of transducers 111 fabricated on a substrate 113, and a plurality of flexible interposers 115. In an exemplary embodiment, interposers 115 include a first interposer 112 and a second interposer 114, wherein first interposer 112 is interchangeable with second interposer 114. Additionally, first interposer 112 includes a first multilayer interconnect system and second interposer 114 includes a second multilayer interconnect system configured differently than the first multilayer interconnect system. For example, interposer 112 and interposer 114 include the same input/output connections to couple to substrate 113 and electronic device 117, but the multilayer interconnect system includes different wiring configurations. Sensor array kit 110 also includes an electronic device 117, such as but not limited to a signal processor circuit, configured to removably couple to at least one of substrate 113 and interposers 115.

Figure 12:
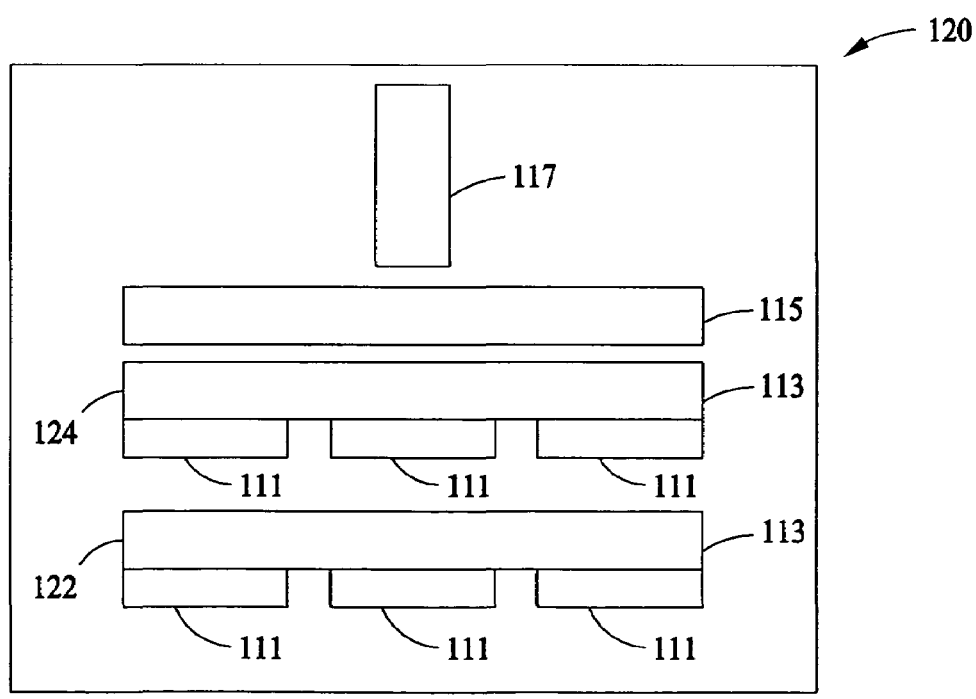
FIG. 12 is a top plan view of a second transducer array kit.

FIG. 12 is a top plan view of a sensor array kit 120. In an exemplary embodiment, sensor array kit 110 includes a plurality of substrates 113 including a plurality of transducers 111 fabricated on a substrate 113, and a flexible interposer 115. In an exemplary embodiment, sensor array kit 120 includes a first substrate 122 including a plurality of transducers 111, and a second substrate 124 including a plurality of transducers 111, wherein first substrate 122 is interchangeable with second substrate 124. Sensor array kit 120 also includes an electronic device 117, such as but not limited to a signal processor circuit, configured to removably couple to at least one of substrate 113 and interposer 115.

Figure 13:
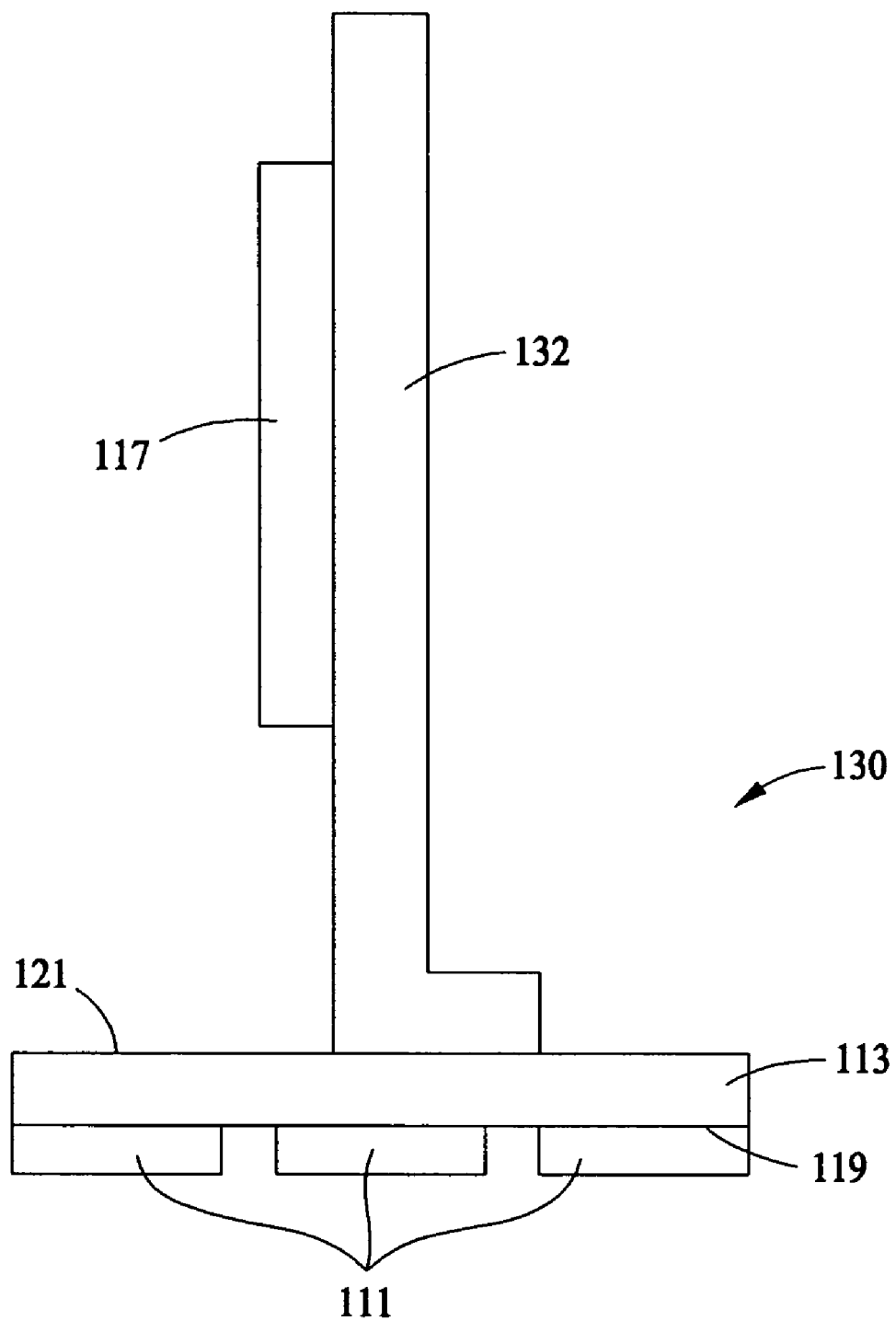
FIG. 13 is a side view of an alternate embodiment of a portion of a tileable sensor array.

FIG. 13 is a side view of an alternate embodiment of a portion of a tileable sensor array 130. In an exemplary embodiment, tileable sensor array 130 includes a plurality of transducers 111 fabricated on a substrate 113. Sensor array 130 also includes a flexible printed circuit board 132 removably coupled to substrate 113 and an electronic device 117. In one embodiment, flexible printed circuit board 132 includes an approximately ninety-degree bend configured to couple to substrate second side 121. In another embodiment, flexible printed circuit board 132 includes a bend between approximately zero-degrees and approximately ninety-degrees such that flexible printed circuit board 132 extends approximately obliquely from substrate second side 121. In use, electronic device 117 is configured to transmit signals to plurality of transducers 111 fabricated on a substrate first side 119, and receive signals from plurality of transducers 111 fabricated on substrate first side 119. For example, sensor array 130 can be configured as a transmitter or a receiver using the desired transducers 111.

In use, a sensor array 130 facilitates configuring a plurality of sensor arrays 130 adjacent to each other such that a larger image area or volume can be imaged. For example, by locating the device I/O pads on the back of a substrate, a plurality of sensor arrays 130 can be butted, side-by-side, in both the x and z axis, to form continuous arrays, tiles, and panels, etc. Further, an electrical contact to sensor arrays 130 can be effected by using a high density electrical interconnect system such as a flexible interconnect, e.g., metal-on-polyimide film, etc., I/O pads attached to the back of sensor array 130 thereby facilitating transmission of signals from the sensor arrays to the system as well as the installation and removal of sensor arrays 130 without interference or impact on adjacent system components.

Further, a high density package including a plurality of signal processors, analog-to-digital converters, or other ancillary electronics could be located on, at, or near the sensor 130 to facilitate improving electrical performance and system function. By locating these electrical functions and components in close proximity to the sensor or device arrays, system function and performance may be improved. These improvements result from reduced signal path lengths for component-to-component and component-to-system interconnect as well as a reduction in the number of system interconnects as effected by the ability to multiplex digital signals available following conversion from their analog counterparts detected using the sensor pixels, channels, etc. Additionally, since the electronics are positioned at an angle from the substrate, a greater quantity of electronics can be electrically coupled to the sensor array since the printed circuit board can be increased to any desired length to allow coupling of any desired quantity of electronics. More specifically, the flexible printed circuit board can be fabricated with a surface area greater than the surface area of the substrate.

Additionally, using sensor array 130, including electrical contacts located on its back, e.g., a sensor, and an interconnect, e.g., metal-on-polyimide flexible film attached to the substrate I/O pads facilitates increasing a quantity of I/O connections, since device I/O's are often configured either in single, linear, or area pad arrays, with an area array offering the greatest density of I/O connections. For the density of I/O connections effected by area arrays, at fine pitch (less than 1 mm), utilizing a flexible interconnect facilitates achieving a high performance, highly reliable electrical connection. Further, by attaching electronic device 117, at, or near the sensor, additional improvements may be achieved in the areas of electrical and functional performance, reduction of noise, and reduction of system I/O connections. These improvements are realized as a result of reduced interconnect lengths, e.g., the interconnect from sensor to system amplification, and the capacity for signal amplification, processing, conditioning, etc., implemented prior to transmitting the signals to the system, in parallel or serial format. Also, environmental and electrical shielding to protect signals from undesired interference and signal degradation may be included by means of embedding or affixing the appropriate materials, e.g., tungsten, diamond-like-carbon, copper, etc., to the backside of the sensor, metal-on-polyimide film, or miniature packages attached to the interconnect system(s) or included in the sensor system packaging.

Having interconnected and packaged system components to effect a miniature package with a backside I/O connection, as described above, the sensors could then be arranged in two-dimensional arrays. These two dimensional arrays, made possible by the lack of I/O connections situated or located at the device periphery, can be configured to any size or dimension, relative to the quantity and arrangement of rows and columns of individual sensors, thus providing for desired structures compatible with applications in imaging or characterizing desired physical areas or volumes of physical objects, energy fields, etc.

In another implementation, a rigid, semi-rigid, or flexible interposer can be attached to the sensor back or top located I/O connections prior to assembly or attachment of ancillary or system electronics. This interposer may serve to reconfigure, fan-in, or fan-out I/O connections as well as provide shielding, embedded or affixed, and provide a substrate or mounting base for system electronics, components, etc. Furthermore the interposer could be constructed to satisfy desired mechanical or thermal performance needs.

In some configurations of the present invention, high precision alignment of elements of a tileable sensor array is achieved. For example, an array of compressible, low-profile alignment structures, such as those found on mating surfaces of LEGO® bricks, is bonded to sensor arrays which are then tiled to form a detector array. These alignment structures may be either recessed or extrude from the surface. The surface is made from a material that is transparent to the energy being transmitted to the sensor array. The sensor array is formed by compression fitting each element, using the attached alignment structures, into a monolithic mating surface for the entire array. In this aspect, configurations of the present invention in either one dimension or two dimensions are enabled, and replacement of individual sensor arrays is facilitated, thereby enabling field repair of a detector array by replacement of sensor arrays.

Figure 14:
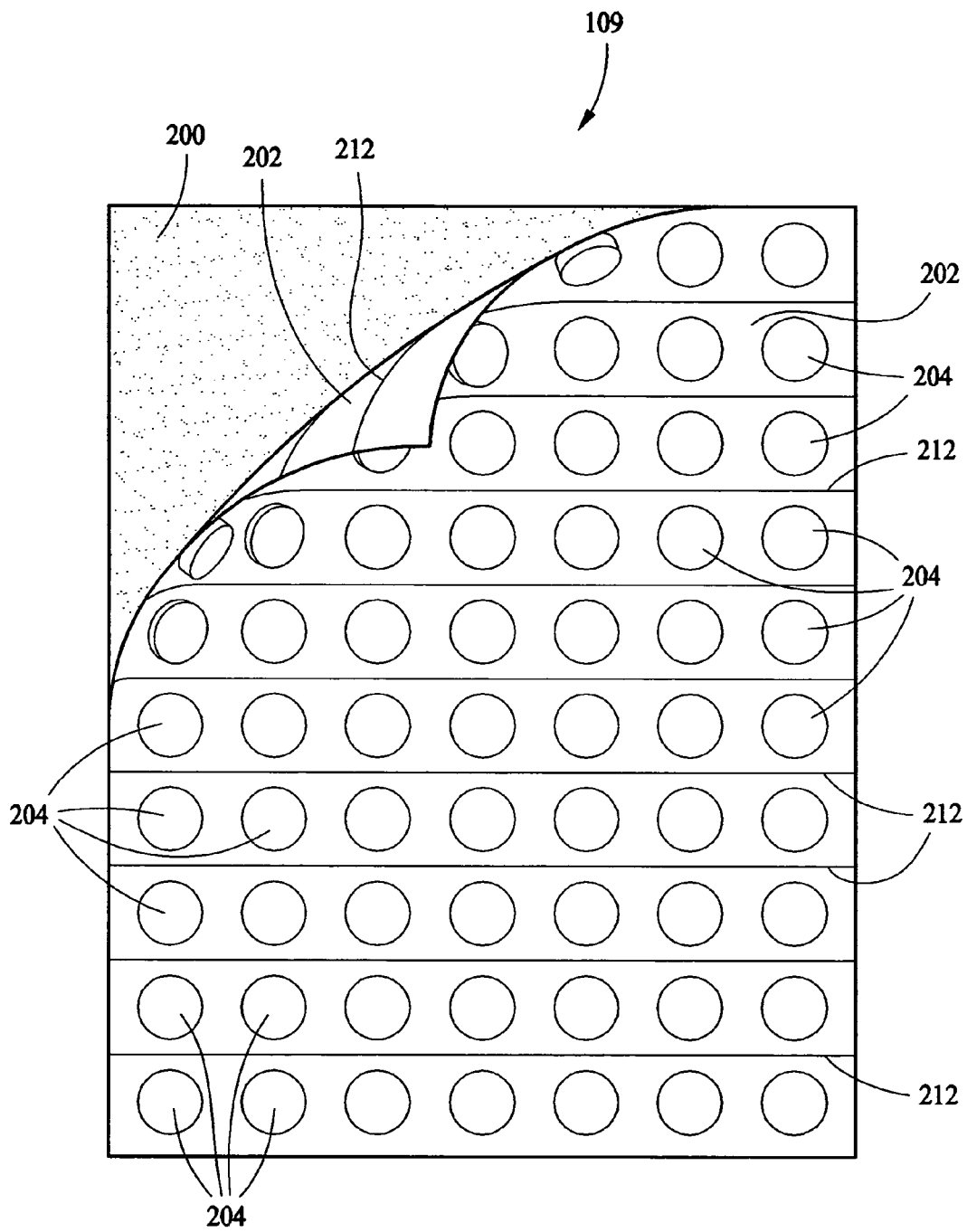
FIG. 14 is a top pictorial view of a configuration of a sensor array having an alignment structure affixed to an active surface thereof.

For example and referring to FIG. 14, an active side 200 of a sensor array 109 having one or more sensors is covered with a positioning structure 202 having a raised alignment structure, e.g., studs 204 on precision aligned centers. For example, studs 204 are 5 mm in diameter, with centers spaced 8 mm apart, with spacings and diameters having a 15 micron tolerance. The stud sizes and centers can be different in other configurations and can be selected in accordance with the size of active side 200. The dimensions and tolerances described above are practical for various configurations of the present invention; however, LEGO® blocks manufactured as toys have tolerances as small as 2 microns. The one or more sensors are configured to produce a signal when a particular form of energy is detected. In various configurations of the present invention, the particular form of energy comprises x-rays, but can be a different form of energy in other configurations, such as visible light energy or sound energy. In some configurations in which the particular form of energy comprises x-rays, the sensor comprises an x-ray scintillation detector.

Positioning structure 202 may, for example, comprise a rubber or plastic composition that is shaped in any suitable manner (e.g., by molding) and affixed (for example, using glue or other adhesive or otherwise bonded) to an active side 200 of sensor array 109. The curling of positioning structure 202 in FIG. 14 is intended to show only one manner in which positioning structure 202 can be applied or removed, and to permit illustration of raised studs 204. It is not required that positioning structure 202 be so flexible as to permit such curling. For example, in some configurations, positioning structure 202 can comprise acrylonitrile-butadiene-styrene (ABS), shaped graphite, or shaped aluminized graphite, glued onto sensor array 109. (The terms "studs" and "tubes" are intended to encompass elements that perform the same function as the studs and tubes of LEGO® blocks, even if such elements are not circular in shape.) In some configurations, positioning structure 202 does not extend beyond edges of active side 200 of sensor array 109, which advantageously allows sensor arrays 109 to be mounted in an abutting alignment on a mounting structure.

The composition of positioning structure 202 is transparent or nearly transparent to the particular form of energy that is to be sensed by the sensor on active side 200 of sensor array 109. For example, in some configurations in which sensor array 109 is part of a CT detector array, active side 200 comprises a scintillator deposited over an array of photodiodes, and the particular form of energy to be sensed is x-ray energy. Suitable materials for positioning structure 202 in this case include any compressible material transparent to x-rays. For example, metal-free plastics and rubbers are suitable, as is graphite. Aluminized graphite can be used for positioning structure 202 to reflect visible light generated by x-rays impinging on the scintillator material back to photodiodes on a substrate of sensor array 109.

Figure 15:
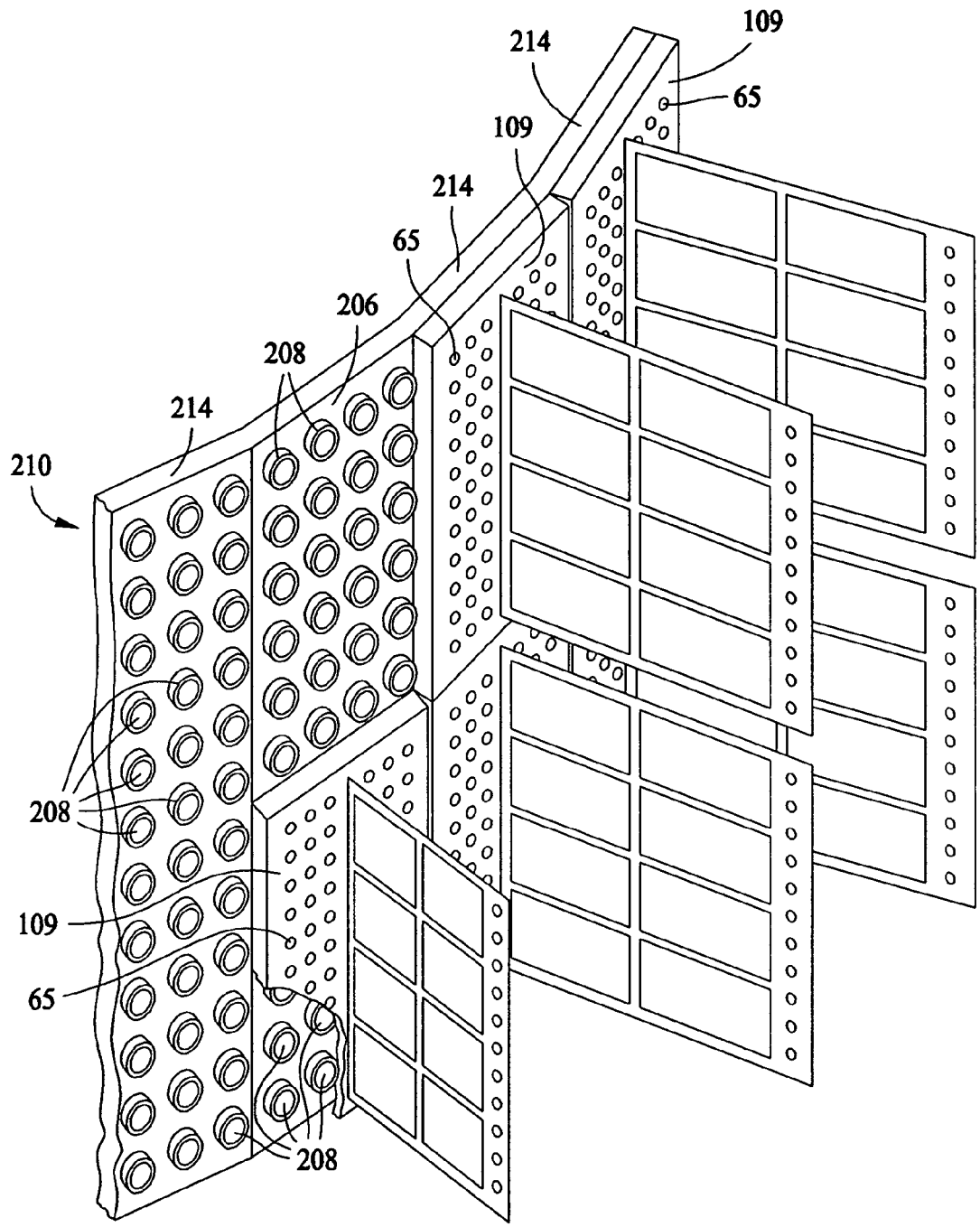
FIG. 15 is a partial cut-away pictorial view of a partially assembled configuration of a detector array of the present invention.

In some configurations and referring to FIG. 15, positioning structure 202 engages with and is held in place by a corresponding surface of a mounting structure 210. (Positioning structure 202 is not shown in FIG. 15 but is on surfaces 200 of sensor arrays 109. Surfaces 200 are not visible in FIG. 15, even in the cut-away section, because they are turned towards surfaces 206 of mounting structure 210.) In some configurations, mounting structure 210 is a monolithic structure having a plurality of planar segments 214 that meet at angles so that mounting structure 210 approximates an ideal detector array arc. (The present invention does not require mounting structure 210 to have a plurality of planar segments 214, however. For example, various configurations of flat panel detector arrays comprise only a single planar segment 214.) Each face 206 of a planar segment 214 that is configured for placement of at least one sensor array has thereon a plurality of precision aligned and dimensioned tubes 208 that compressibly and frictionally engages with studs 204 on positioning structure 202 of sensor array 109. Mounting structure 210 is also transparent or nearly transparent to the energy that is to be sensed by active side 200 of sensor array 109. For example, mounting structure 210 can comprise the same materials used for positioning structure 202. (FIGS. 14 and 15 are for illustration only and do not necessarily accurately represent the actual number of studs 204 and tubes 208 on matching surfaces.)

In some configurations, the detector array is an x-ray detector array, and sensor array 109 is a scintillation detector. In x-ray detector configurations, either mounting structure 210 and/or positioning structure 202 may comprise at least one collimator blade, for example, collimator blades 212 illustrated in FIG. 14. In some configurations, collimator blades 212 are embedded in either or both mounting structure 210 and/or positioning structure 202. (Although collimator blades 212 in FIG. 14 are shown only in regions of positioning structure 202 only between rows of stud-like structure 204, there is no requirement that the blades not pass through structures 204. Moreover, the spacing of collimator blades 212 in various configurations is determined by the spacing of sensors in sensor array 109 rather than stud-like structures 204.) In some configurations, mounting structure 210 has flat faces and tubes 208 are on a structure that is glued onto the flat faces, in a manner similar to that described with respect to positioning structure 202 and surface 200 of sensor array 109.

Although mounting structure 210 is shown and described as having a plurality of protruding tube-like structures 208 and positioning structure 202 is shown and described as having a plurality of protruding stud-like structures 204, the locations of tube-like structures 208 and stud-like structures 204 can be reversed. Thus, in some configurations, positioning structure 202 has a plurality of stud-like structures 208 and mounting structure 210 has a plurality of stud-like structures 204. In either case, stud-like structures 204 and tube-like structures 208 compressively and frictionally interlock with one another, holding sensor array 109 to mounting structure 210.

Thus, in some configurations of the present invention, an array of compressible, low-profile alignment structures 204 is provided on the external surface of a sensor array 109 such as an x-ray scintillator array. Alignment structures 204 may be deposited or formed directly on a surface 200 of the scintillator (e.g., as part of a positioning structure 202) or may be a separately molded part, which is subsequently aligned and bonded to detector array side 200. In some configurations, alignment structures 204 are raised, but in other configurations, they are recessed, as are tubes found at the bottom of a LEGO® block. In cases in which alignment structures 204 are recessed, the perimeter of positioning structure 202 (or surface 200 itself) can comprise a wall around the alignment structures. The wall aids in aligning and positioning sensor array 109 on mounting structure 210. In some configurations, a structure 202 is molded from a material transparent to x-rays. A composite structure 202 in which x-ray opaque materials (e.g., collimator blades, not shown in the Figures) are embedded in the transparent positioning structure 202 is used in some configurations. The maximum dimensions of each positioning structure 202 is the same as side 200 of scintillator array 109, so that mounting does not require an oversized backing plate such as the oversized ceramic backing plate used in some known CT imaging systems.

In some configurations in which collimator blades are not embedded in transparent positioning structure 202, each sensor array 109 is aligned to a x-ray collimator structure, as well as to neighboring sensor arrays 109 in a detector array. To achieve positioning accuracy of sensor array 109 and a collimator rail, a complementary stud or tube mounting structure 210 is added to a collimator rail. Complementary mounting structure 210 is also essentially transparent to the particular energy that the sensors of sensor array 109 are intended to detect. Use of molded plastic mounting structures 210 and a custom mold facilitates matching the curved design of a CT collimator rail while still allowing for positioning accuracy between the collimator rail and sensor array 109. Sensor arrays 109 are assembled using a compression fit between the studs or tubes and the complementary monolithic mounting structure 210 on the collimator rail. Additional retaining devices (not shown) may be used subsequent to alignment to lock sensor arrays 109 into place, but additional retaining devices are not required to practice the present invention. Two dimensional arrays of sensor arrays 109 can readily be assembled by providing an appropriately dimensioned mounting structure 210.

In some configurations, positioning structure 202 is bonded, affixed or glued directly onto a scintillator coating forming side 200 of sensor array 109. This scintillator coating in some configurations is grown directly on top of a photodiode array on sensor array 109. Some configurations of the present invention interpose one or more additional protective or reflective layers between positioning structure 202 and the scintillator coating forming side 200 of sensor array 109. For some types of sensor arrays 109, positioning structure 202 can be part of the sensor array itself (not necessarily glued, bonded or otherwise affixed thereto), such that sensor array 109 includes alignment structures 204.

It will be appreciated that configurations of the present invention utilizing stud-and tube coupling facilitate insertion and extraction of sensor arrays 109 with high dimensional accuracy. Use of a positioning structure 202 that does not extend beyond the edges of sensor array 109 and the precise alignment of sensor arrays 109 enables insertion and extraction of sensor arrays 109 in a two-dimensional detector array. The ease with which sensor arrays 109 can be inserted with high dimensional accuracy and extracted permit sensor arrays 109 to be field-replaceable units in devices such as CT imaging systems. Moreover, configurations of detector arrays such as detector array 16 in a CT imaging apparatus 10 can be supplied in kit form for assembly, so that sensor arrays 109 can be compressionally and frictionally mounted by hand in a mounting structure 210 to produce a precision-aligned detector array. (Compressionally and frictionally mounting a sensor array can be accomplished in many configurations by merely pressing the sensor array onto the alignment structure.) Such detector arrays can comprise both plurality of rows and a plurality of columns of sensor arrays 109.

Repair of some configurations of detector arrays of the present invention can be accomplished by disengaging a first sensor array 109 from a mounting structure 210, and compressionally and frictionally engaging a second sensor array 109 in place of the first sensor array. The disengaging and replacement need not require special tools, and can effectively and easily be accomplished in arrays such as x-ray detector arrays and detector arrays in CT imaging apparatus.

While the invention has been described in terms of various specific embodiments, those skilled in the art will recognize that the invention can be practiced with modification within the spirit and scope of the claims.

What is claimed is:

1. A sensor array having an active side and comprising:
   at least one sensor on the active side configured to produce a signal when a particular form of energy is detected; and
   a positioning structure on the active side essentially transparent to the particular form of energy, said positioning structure comprising a plurality of spaced compressible posts or tubes configured to compressively and frictionally engage with a complementary mounting structure.

2. A sensor array in accordance with claim 1 wherein said at least one sensor comprises an x-ray scintillation detector.

3. A sensor array in accordance with claim 2 wherein said positioning structure comprises molded plastic.

4. A sensor array in accordance with claim 2 wherein said positioning structure comprises rubber.

5. A sensor array in accordance with claim 2 wherein said positioning structure comprises acrylonitrile-butadiene-styrene (ABS).

6. A sensor array in accordance with claim 2 wherein said positioning structure comprises graphite.

7. A sensor array in accordance with claim 2 wherein said positioning structure comprises aluminized graphite.

8. A sensor array in accordance with claim 1 wherein said positioning structure is glued onto the active side.

9. A sensor array in accordance with claim 8 wherein said positioning structure does not extend beyond edges of the active side of said detector array.

10. A sensor array in accordance with claim 1 wherein said at least one sensor comprises a plurality of x-ray scintillation detectors, and said positioning structure further comprises at least one collimator blade.

11. A sensor array in accordance with claim 10 wherein said positioning structure comprises molded plastic.

12. A sensor array in accordance with claim 1 wherein said positioning structure is affixed to the active side of the sensor array.

13. A detector array kit comprising:
    at least one sensor array having an active side and comprising at least one sensor on the active side configured to detect a particular form of energy, said at least one sensor array further comprising a positioning structure on the active side that is essentially transparent to the particular form of energy, said positioning structure comprising a plurality of spaced compressible posts or tubes configured to compressively and frictionally engage with a complementary mounting structure; and
    a complementary mounting structure essentially transparent to the particular form of energy.

14. A detector array kit in accordance with claim 13 wherein said detector array is an x-ray detector array.

15. A detector array kit in accordance with claim 14 wherein said positioning structure and said complementary mounting structure comprise molded plastic.

16. A detector array kit in accordance with claim 14 wherein said positioning structure comprises acrylonitrile-butadiene-styrene (ABS).

17. A detector array kit in accordance with claim 14 wherein said positioning structure comprises rubber.

18. A detector array kit in accordance with claim 14 wherein said positioning structure comprises graphite.

19. A detector array kit in accordance with claim 14 wherein said positioning structure comprises aluminized graphite.

20. A detector array in accordance with claim 13 wherein said at least one sensor array is compressively and frictionally mounted on said complementary mounting structure.

21. A detector array kit in accordance with claim 13 wherein said complementary mountings structure is configured to mount a plurality of rows and a plurality of columns of said sensor arrays.

22. A detector array kit in accordance with claim 21 wherein said plurality of rows and plurality of columns of said sensor arrays are compressionally and frictionally mounted on said complementary mounting structure.

23. A detector array kit in accordance with claim 13 wherein said positioning structure is affixed to the active side of the sensor array.

24. A detector array kit comprising:
    a plurality of sensor arrays each having an active side and comprising at least one sensor on the active side configured to detect a particular form of energy, said sensor arrays each further comprising a positioning structure on the active side that is essentially transparent to the particular form of energy, said positioning structure comprising a plurality of spaced compressible posts or tubes configured to compressively and frictionally engage with a complementary mounting structure; and a unitary complementary mounting structure essentially transparent to the particular form of energy and having a plurality of planar segments that meet at angles.

25. A detector array kit in accordance with claim 24 wherein said detector array is an x-ray detector array.

26. A detector array in accordance with claim 25 wherein said sensor arrays are compressively and frictionally mounted on said complementary mounting structure.

27. A detector array in accordance with claim 26 having a plurality of both rows and columns of sensor arrays.

28. A computed tomograpic imaging apparatus comprising:
   a rotating gantry;
   an x-ray source on the rotating gantry configured to project an x-ray beam through an object being imaged;
   a table configured to support the object in the x-ray beam; and
   a detector array on the rotating gantry configured to detect x-rays passing through the object, said detector array comprising
      a plurality of sensor arrays each having an active side and comprising at least one x-ray sensor on the active side configured to detect x-rays, said sensor arrays each further comprising a positioning structure on the active side that is essentially transparent to the particular form of energy, said positioning structure comprising a plurality of spaced compressible posts or tubes configured to compressively and frictionally engage with a complementary mounting structure; and
      a unitary complementary mounting structure essentially transparent to x-rays and having a plurality of planar segments that meet at angles.

29. An apparatus in accordance with claim 28 wherein said unitary complementary mounting structure has a plurality of planar segments that meet at angles.

30. An apparatus in accordance with claim 29 wherein said detector array comprises both a plurality of rows and a plurality of columns of sensor arrays.

31. A method for repairing a detector array comprising:
   disengaging a first sensor array having an active side and at least one sensor on the active side configured to produce a signal when a particular form of energy is detected, and a positioning structure on the active side that is essentially transparent to the particular form of energy, said positioning structure comprising a plurality of spaced compressible posts or tubes compressively and frictionally engaged with a complementary mounting structure essentially transparent to the particular form of energy; and
   compressively and frictionally engaging a second sensor array in place of the first sensor array.

32. A method in accordance with claim 31 wherein said detector array is in a computed tomographic imaging apparatus.

33. A method in accordance with claim 31 wherein said detector array is an x-ray detector array.

* * * * *